(12) United States Patent
Lee et al.

(10) Patent No.: US 7,125,442 B2
(45) Date of Patent: Oct. 24, 2006

(54) LIGHTFAST ADDITIVE HAVING UV-ABSORBING MOIETY AND INK COMPOSITION INCLUDING THE SAME

(75) Inventors: Kyung-hoon Lee, Gyeonggi-do (KR); Seung-min Ryu, Gyeonggi-do (KR); Yeon-kyoung Jung, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 102 days.

(21) Appl. No.: 10/851,161

(22) Filed: May 24, 2004

(65) Prior Publication Data
US 2004/0237837 A1   Dec. 2, 2004

(30) Foreign Application Priority Data
May 27, 2003   (KR) ...................... 10-2003-0033848

(51) Int. Cl.
| | | |
|---|---|---|
| C09D 11/00 | (2006.01) | |
| C07C 69/73 | (2006.01) | |
| C07C 69/76 | (2006.01) | |
| C07C 219/28 | (2006.01) | |
| C07D 207/28 | (2006.01) | |
| C07D 213/55 | (2006.01) | |
| C07D 277/06 | (2006.01) | |
| C07D 333/24 | (2006.01) | |

(52) U.S. Cl. ............................... 106/31.43; 106/31.47; 106/31.49; 106/31.58; 106/31.77; 106/31.78; 106/31.88; 546/342; 548/200; 548/534; 549/79; 560/38; 560/52

(58) Field of Classification Search ................ 546/342; 548/200, 534; 549/79; 560/38, 52; 106/31.43, 106/31.47, 31.49, 31.58, 31.77, 31.78, 31.86
See application file for complete search history.

(56) References Cited

U.S. PATENT DOCUMENTS

| | | | | |
|---|---|---|---|---|
| 3,785,827 | A * | 1/1974 | Piller et al. ................. 430/512 |
| 4,058,552 | A * | 11/1977 | Mieville ...................... 560/52 |
| 5,041,545 | A * | 8/1991 | Myers ......................... 540/450 |
| 5,407,971 | A * | 4/1995 | Everaerts et al. ............. 522/35 |
| 6,045,586 | A * | 4/2000 | Bacher et al. ............. 8/115.59 |
| 6,346,595 | B1 | 2/2002 | O'Lenick, Jr. ............... 528/29 |
| 6,811,596 | B1 * | 11/2004 | Bedford et al. .......... 106/31.29 |

FOREIGN PATENT DOCUMENTS

| | | | |
|---|---|---|---|
| EP | 303283 | * | 2/1989 |
| JP | 05-194400 | * | 8/1993 |

OTHER PUBLICATIONS

Soper et al., J. Am. Chem. Soc., 70, 2849-2855, 1948.*
Schvartzapel et al., J. Med. Chem., 41, 2314-2322, 1997.*
Liu et al., Bioconjugate Chem., 11, 755-761, 2000.*
MacLeay et al., Chemical Abstracts, 122:215586, 1995.*
Kashiwai et al., Chemical Abstracts, 117:233587, 1992.*
Massolini et al., Chemical Abstracts, 106:151469, 1987.*
Bayles et al., Chemical Abstracts, 86:106144, 1977.*
Short et al., Chemical Abstracts, 62:10355e-g, 1965.*
U.S. Appl. No. 10/851,124, filed May 24, 2004, Kyung-hoon et al.

* cited by examiner

Primary Examiner—Fiona T. Powers
(74) Attorney, Agent, or Firm—Staas & Halsey LLP

(57) ABSTRACT

A lightfast additive and an ink composition including the same include a benzophenone moiety for lightfastness and a moiety for wettability and the ability to stabilize a colorant, wherein the two moieties are covalently bonded. The lightfast additive may exhibit effective ultraviolet (UV) light absorption capacity, effective wettability, and an ability to stabilize a colorant. The ink composition utilizing the light fast additive thus has an improved lightfastness and long-term storage stability.

18 Claims, No Drawings

LIGHTFAST ADDITIVE HAVING UV-ABSORBING MOIETY AND INK COMPOSITION INCLUDING THE SAME

CROSS-REFERENCE TO RELATED APPLICATIONS

This application claims the priority of Korean Patent Application No. 2003-33848, filed on May 27, 2003, in the Korean Intellectual Property Office, the disclosure of which is incorporated herein in its entirety by reference.

BACKGROUND OF THE INVENTION

1. Field of the Invention

The present invention relates to a lightfast additive and an ink composition including the same, and more particularly, to a lightfast additive that provides lightfastness to a colorant and stabilizes the colorant, and an ink composition including the lightfast additive.

2. Description of the Related Art

In general, ink compositions for inkjet printing contain a colorant, such as a dye or pigment, a stabilizer and a dispersing agent, which respectively stabilize and disperse the colorant, an organic solvent, and a wetting agent that prevents drying of the ink composition.

Prints obtained using such ink compositions may be exposed to air, visible light, and ultraviolet (UV) rays over a period of time. UV rays, which have a higher energy level than visible light, raise more serious problems. For example, the whiteness of a printing medium, such as paper, deteriorates and changes to yellow. In addition, color images printed using an ink composition that have poor lightfastness are liable to bleach or discolor. To solve these problems, a lightfast additive that blocks or absorbs UV light has been added to ink compositions.

U.S. Pat. No. 6,346,595 discloses the use of a large molecular weight silicon compound as a lightfast additive. However, this large molecular weight silicon compound exhibits poor miscibility with other components of an ink composition and, due to the large molecular weight, greatly affects the physical properties, for example, the viscosity, of the composition even when the amount of the silicon compound is slightly changed. Accordingly, it is difficult to adjust the amount of the additive used. In addition, although the silicone polymer includes hydrophilic groups in its molecular structure, the hydrophilic group content in the silicone polymer is insufficient to dissolve the compound in water, and more time is required to dissolve the compound. Furthermore, the UV absorbing additive may react with a colorant or other additives in the composition when stored over an extensive period of time, resulting in phase separation and deterioration of long-term storage stability.

SUMMARY OF THE INVENTION

The present invention provides a lightfast additive that minimizes the above-listed problems.

The present invention provides an ink composition including the lightfast additive.

In one aspect, the present invention provides a benzophenone derivative of formula (1) below:

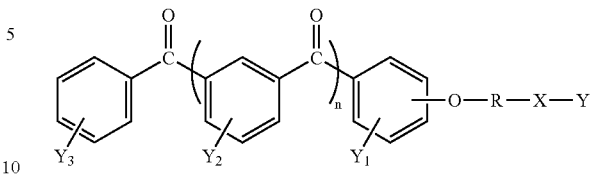

(1)

wherein $Y_1$ is one selected from the group consisting of a H, a OH, an $N(R_1)(R_2)$, a SH, and a $C_1$–$C_{30}$ heteroalkyl group; each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group; R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group; X is a linker selected from the group consisting of —O—, —CO—, —$NR_1$—, —N=N—, —S—, —C(=O)$NR_1$—, —$NR_1$C(=O)—, —$SO_2$—, —$SO_3$—, —COO—, —OCO—, —C(=S)—O—, —OC(=S)—, —CO—O—CO—, —CO—S—O—, —CO—$NR_1$—CO—, —C(=S)—O—C(=S)—, —C(=S)—S—C(=S)—, —C(=S)—$NR_1$—C(=S)—, —O—P(=O)(OH)—O—, and —O—P(OH)—O—; Y is selected from the group consisting of a substituted or unsubstituted $C_1$–$C_{20}$ alkyl group having 1 to 10 hydroxyl groups, —$N(R_1)(R_2)$, —$NHN(R_1)(R_2)$, —$(CH_2)_m$—$N(R_1)(R_2)$, a substituted or unsubstituted $C_2$–$C_{20}$ hydroxyalkyloxyalkyl group, a substituted or unsubstituted $C_3$–$C_{10}$ lactone group, a substituted or unsubstituted $C_3$–$C_{10}$ lactame group; a substituted or unsubstituted $C_3$–$C_{30}$ heteroaryl group, a substituted or unsubstituted $C_4$–$C_{30}$ heteroarylalkyl group, a substituted or unsubstituted $C_5$–$C_{30}$ hetroarylalkenyl group, and a substituted or unsubstituted $C_3$–$C_{10}$ heterocycloalkyl group; and each of $R_1$ and $R_2$ is independently one of a hydrogen atom and a $C_1$-$C_6$ alkyl group; and m and n are independently integers from 0 to 6.

In another aspect, the present invention provides a lightfast ink composition comprising; a colorant; at least one of the benzophenone derivatives of formula (1) above; and an aqueous medium.

Additional aspects and/or advantages of the invention will be set forth in part in the description which follows and, in part, will be obvious from the description, or may be learned by practice of the invention.

DETAILED DESCRIPTION OF THE PREFERRED EMBODIMENTS

Reference will now be made in detail to the embodiments of the present invention, examples of which are illustrated in the accompanying drawings, wherein like reference numerals refer to the like elements throughout. The embodiments are described below to explain the present invention by referring to the figures.

Embodiments of a lightfast additive and an ink composition including the same according to embodiments of the present invention will be described in detail.

The present invention provides a lightfast additive that is a benzophenone derivative of formula (1) below. The benzophenone derivative of formula (1) may exhibit effective ultraviolet (UV) light absorption capacity, effective wettability, and an ability to stabilize a colorant. Accordingly, an ink composition including the benzophenone derivative has longer-storage stability and improved lightfastness.

(1)

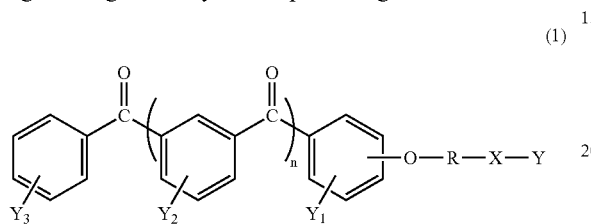

In formula (1), $Y_1$ is one selected from the group consisting of a H, a OH, an $N(R_1)(R_2)$, a SH, and a $C_1$–$C_{30}$ heteroalkyl group; each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group; R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group; X is a linker selected from the group consisting of —O—, —CO—, —NR$_1$—, —N=N—, —S—, —C(=O)NR$_1$—, —NR$_1$C(=O)—, —SO$_2$—, —SO$_3$—, —COO—, —OCO—, —C(=S)—O—, —OC(=S)—, —CO—O—CO—, —CO—S—CO—, —CO—NR$_1$—CO—, —C(=S)—O—C(=S)—, —C(=S)—S—C(=S)—, —C(=S)—NR$_1$—C(=S)—, —O—P(=O)(OH)—O—, and —O—P(OH)—O—; Y is selected from the group consisting of a substituted or unsubstituted $C_1$–$C_{20}$ alkyl group having 1 to 10 hydroxyl groups, —N(R$_1$)(R$_2$), —NHN(R$_1$)(R$_2$), —(CH$_2$)$_m$—N(R$_1$)(R$_2$), a substituted or unsubstituted $C_2$–$C_{20}$ hydroxyalkyloxyalkyl group, a substituted or unsubstituted $C_3$–$C_{10}$ lactone group, a substituted or unsubstituted $C_3$–$C_{10}$ lactame group; a substituted or unsubstituted $C_3$–$C_{30}$ heteroaryl group, a substituted or unsubstituted $C_4$–$C_{30}$ heteroarylalkyl group, a substituted or unsubstituted $C_5$–$C_{30}$ heteroarylalkenyl group, and a substituted or unsubstituted $C_3$–$C_{10}$ heterocycloalkyl group; each of R$_1$ and R$_2$ is independently one of a hydrogen atom and a $C_1$–$C_6$ alkyl group; and m and n are independently integers from 0 to 6.

As is apparent from formula (1) above, the benzophenone derivative according to embodiments of the present invention includes a benzophenone derivative with a non-complex structure and a compound having moieties capable of enhancing wettability and the stability of a colorant, which are bound together via the linker X. The linker X may be an amide bond, an ester bond, a carbonyl bond, a sulfonyl bond, or the like. In other words, the benzophenone derivative of formula (1) is synthesized by a chemical reaction between the compound having the moieties and a benzophenone compound of formula (2) below, which has a relatively non-complex structure.

(2)

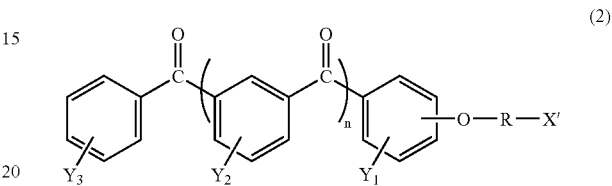

In formula (2), $Y_1$, $Y_2$, $Y_3$, n, and R are the same as in formula (1); and X' is a reactive functional group that is selected from the group consisting of a carboxyl group, a hydroxyl group, an amino group, a sulfonic acid group, and a phosphoric acid group, and so forth.

As illustrated in reaction schemes (1) through (4) below, the benzophenone derivative of formula (1) according to embodiments of the present invention is formed by condensation between a reactive functional group, such as a carboxyl group, a hydroxyl group, an amino group, a sulfonic acid group, and a phosphoric acid group, which are present in the molecular structure of the compound including the moieties and the reactive functional group X', such as a carboxyl group, a hydroxyl group, a amino group, a sulfonic acid group, and a phosphoric acid group, which are present in the molecular structure of the benzophenone derivative structure of formula (2).

Reaction scheme (1)

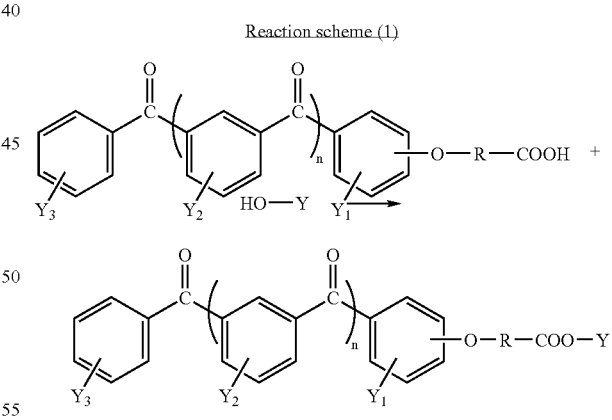

Reaction scheme (2)

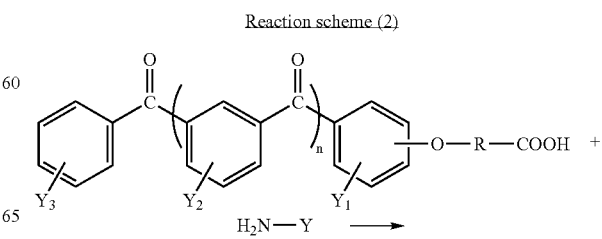

-continued

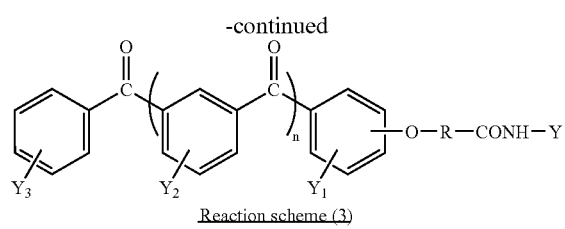

Reaction scheme (3)

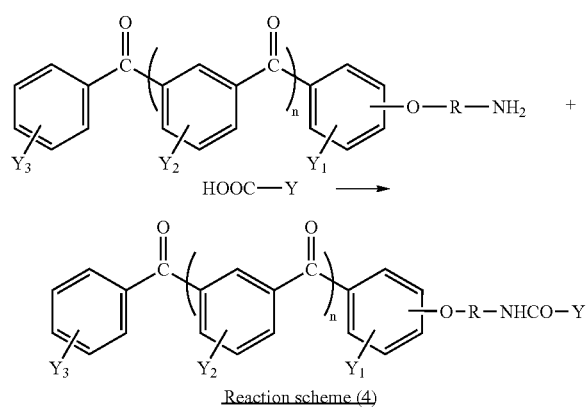

Reaction scheme (4)

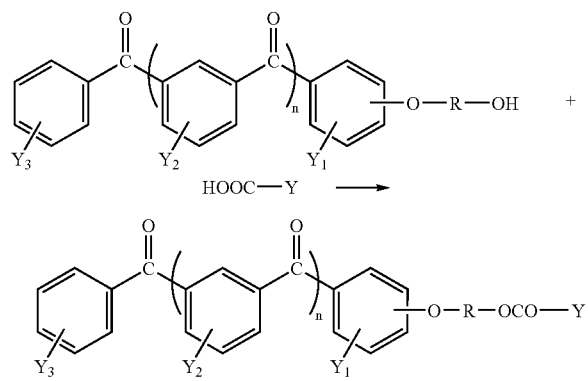

In reaction schemes (1) through (4) above, $Y_1$, $Y_2$, $Y_3$, Y, n, and R are the same as in formula (1). Compounds which are chemically bound with the benzophenone derivative of formula (2) and include moieties capable of improving wettability and the stability of a colorant as described above are expressed as HO—Y, $H_2$N—Y, and HOOC—Y in reaction schemes (1) through (4).

As described above, in formulas (1) and (2), $Y_1$ is one selected from the group consisting of a H, a OH, an $N(R_1)(R_2)$, a SH, and a $C_1$–$C_{30}$ heteroalkyl group, where each of $R_1$ and $R_2$ in the group of $N(R_1)(R_2)$ is independently a hydrogen atom or a straight or branched $C_1$–$C_6$ alkyl group.

$Y_1$ is a straight or branched heteroalkyl group having 1 to 30 carbon atoms, preferably, 1 to 20 carbon atoms, and more preferably, 1 to 10 carbon atoms. A $C_1$–$C_{30}$ heteroalkyl group for $Y_1$ implies a $C_1$–$C_{30}$ alkyl group including 1 to 3 hetero atoms selected from the group consisting of N, O, P, and S. Specific examples of such a heteroalkyl group include, but are not limited to, an oxymethyl group, an oxyethyl group, an oxypropyl group, a mercaptomethyl group, a mercaptoethyl group, a mercaptopropyl group, and the like. At least one hydrogen atom in the heteroalkyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

As described above, $Y_2$ and $Y_3$ in formulas (1) and (2) are independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group. Each of $R_1$ and $R_2$ in the group of $N(R_1)(R_2)$ is independently a hydrogen atom or a straight or branched $C_1$–$C_6$ alkyl group.

In particular, each of $Y_2$ and $Y_3$ may be a straight or branched alkyl group having 1 to 30 carbon atoms, preferably, 1 to 20 carbon atoms, and more preferably, 1 to 10 carbon atoms. Specific examples of such an alkyl group include, but are not limited to, a methyl group, an ethyl group, an n-propyl group, an isopropyl group, an n-butyl group, an isobutyl group, a sec-butyl group, a t-butyl group, a pentyl group, an iso-amyl group, a hexyl group, a heptyl group, an octyl group, a nonyl group, a decyl group, a dodecyl group, and the like, wherein at least one hydrogen atom in the alkyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

Each of $Y_2$ and $Y_3$ may be a straight or branched heteroalkyl group having 1 to 30 carbon atoms, preferably, 1 to 20 carbon atoms, and more preferably, 1 to 10 carbon atoms. A $C_{10}$–$C_{30}$ heteroalkyl group for each of $Y_1$ and $Y_3$ implies a $C_1$–$C_{30}$ alkyl group including 1 to 3 hetero atoms selected from the group consisting of N, O, P, and S. Specific examples of such a heteroalkyl group include, but are not limited to, an oxymethyl group, an oxyethyl group, an oxypropyl group, a mercaptomethyl group, a mercaptoethyl group, a mercaptopropyl group, and the like. At least one hydrogen atom in the heteroalkyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

Each of $Y_2$ and $Y_3$ may be a straight or branched alkenyl group having 1 to 30 carbon atoms, preferably, 1 to 20 carbon atoms, and more preferably, 1 to 10 carbon atoms. The alkenyl group refers to an alkyl group that includes at least one carbon-carbon double bond in its molecular structure. Specific examples of such an alkenyl group include, but are not limited to, an ethylene group, a propylene group, a butylene group, a hexylene group, an allyl group, and the like. At least one hydrogen atom of the alkenyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

Each of $Y_2$ and $Y_3$ may be a straight or branched alkynyl group having 1 to 30 carbon atoms, preferably, 1 to 20 carbon atoms, and more preferably, 1 to 10 carbon atoms. The alkynyl group refers to an alkyl group that includes at least one carbon-carbon triple bond in its molecular structure. Specific examples of such an alkynyl group include, but are not limited to, an acetinyl group, a propynyl group, and the like. At least one hydrogen atom of the alkynyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

Each of $Y_2$ and $Y_3$ may be an aryl group having 6 to 30 carbon atoms, preferably, 6–18 carbon atoms, and more preferably, 6 to 12 carbon atoms, the aryl group being a hydrocarbon group that includes at least one aromatic ring. Specific examples of such an aryl group include, but are not limited to, aromatic radicals, such as phenyl, naphthyl, biphenyl, tetrahydronaphthyl, indanyl, and the like, with phenyl and naphthyl being preferred. At least one hydrogen atom in the aryl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

A substituted or unsubstituted arylalkyl group for each of $Y_2$ and $Y_3$ may have 7 to 30 carbon atoms, preferably, 7 to 19 carbon atoms, and more preferably, 7 to 13 carbon atoms. Specific examples of such an arylalkyl group include, but are not limited to, benzyl, phenetyl, triphenylmethyl, diphenylmethyl, phenylbutyl, neophyl, and the like. At least one hydrogen atom in the arylalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like. The arylalkyl group for each of $Y_2$ and $Y_3$ may include a carbon-carbon double bond or carbon-carbon triple bond in its alkyl residue, like a styryl group.

A substituted or unsubstituted heteroaryl group for each of $Y_2$ and $Y_3$ may have 3 to 30 carbon atoms, preferably, 3 to 18 carbon atoms, and more preferably, 3 to 12 carbon atoms. The heteroaryl group refers to an aryl group that contains one, two, or three hetero atoms, as atom(s) forming an aromatic ring skeleton, selected from the group consisting of N, O, P, and S, wherein at least one of the hetero atoms may be oxidized or quaternarized into, an N-oxide or a quaternary salt. Examples of such a heteroaryl group include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, an N-oxide and a quaternary salt of the foregoing materials, for example, pyridyl N-oxide, quinolinyl N-oxide, and the like. At least one hydrogen atom in the heteroaryl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

A substituted or unsubstituted heteroarylalkyl group for each of $Y_2$ and $Y_3$ may have 4 to 30 carbon atoms, preferably, 4 to 18 carbon atoms, and more preferably, 4 to 12 carbon atoms. The heteroarylalkyl group refers to an arylalkyl group containing one, two, or three heteroatoms, as atom(s) forming an aromatic ring skeleton, selected from the group consisting of N, O, P, and S. Examples of such a heteroarylalkyl group include, but are not limited to, thienylmethyl, thienylethyl, benzothienylmethyl, benzothienylethyl, pyridylmethyl, pyridylpropyl, pyrazinylmethyl, pyrazinylethyl, pyrimidinylmethyl, pyrimidinylethyl, pyridazinylmethyl, pyridazinylethyl, quinolinylmethyl, quinolinylethyl, quinoxalinylmethyl, quinoxalinyletehyl, imidazolylmethyl, imidazolylethyl, furanylmethyl, furanylethyl, and the like. At least one hydrogen atom in the heteroarylalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

In formula (1) and (2) above, R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group. The alkylene group, alkenylene group, alkynylene group, heteroalkylene group, arylene group, arylenealkylene (or alkylenearylene) group, heteroarylene group, and heteroarylenealkylene (or heteroalkylenearylene) group are divalent radicals incorporated in the middle of compounds, not monovalent radicals positioned at an end of compounds, and correspond to an alkyl group, alkenyl group, alkynyl group, heteroalkyl group, aryl group, arylalkyl group, heteroaryl group, and heteroarylalkyl group, respectively.

An alkylene group for R may be a straight or branched radical having 1 to 30 carbon atoms, preferably, 1 to 20 carbon atoms, and more preferably, 1 to 10 carbon atoms. Specific examples of such an alkylene group include, but are not limited to, a methylene group, an ethylene group, a n-propylene group, an isopropylene group, a n-butylene group, an isobutylene group, a sec-butylene group, a t-butylene group, a n-pentylene group, a sec-pentylene group, a t-pentylene group, a hexylene group, a heptylene group, an octylene group, a nonylene group, a decylene group, a dodecylene group, and the like. At least one hydrogen atom in the heteroarylalkyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

An alkenylene group or alkynylene group for R may have 1 to 30 carbon atoms, preferably, 1 to 20 carbon atoms, and more preferably, 1 to 10 carbon atoms. The alkenylene group and alkynylene group differ from alkylene groups only in that they have at least one carbon-carbon double bond or carbon-carbon triple bond, respectively. At least one hydrogen atom in the alkenylene or alkynylene group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

A heteroalkylene group for R may have 1 to 30 carbon atoms, preferably, 1 to 20 carbon atoms, and more preferably, 1 to 10 carbon atoms. The heteroalkylene group refers to an alkylene group that includes one, two, or three hetero atoms selected from the group consisting of N, O, P, and S. Specific examples of such a heteroalkylene group include an oxymethylene group, an oxyethylene group, an oxypropoxy group, a mercaptomethylene group, a mercaptoethylene group, a mercaptopropoxy group, and the like. At least one hydrogen atom in the heteroalkylene group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

An arylene group for R may have 6 to 30 carbon atoms, preferably, 6 to 18 carbon atoms, and more preferably, 6 to 12 carbon atoms. Specific examples of such an arylene group include, but are not limited to, aromatic groups, such as a phenylene group, a naphthylene group, a biphenylene group, a tetrahydronaphthylene group, an indenylene group, and the like, with the phenylene group, biphenylene group, and nathphylene group being preferred. At least one hydrogen atom in the arylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

An arylenealkylene group for R may have 7 to 30 carbon atoms, preferably, 7 to 19 carbon atoms, and more preferably, 7 to 13 carbon atoms. The arylenealkylene group refers to a divalent radical corresponding to an arylalkyl group and comprises an alkylenearylene group. Specific examples of such an arylenealkylene group include, but are not limited to, a methylenephenylene group, an ethylenephenylene group, a methylenenaphthylene group, an ethylenenaphthylene group, a methylenebiphenylene group, an ethylenebiphenylene group, an n-propylenephenylene group, an isopropylenephenylene group, and the like. At least one hydrogen atom in the arylenealkylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

A heteroarylene group for R may have 3 to 30 carbon atoms, preferably, 3 to 18 carbon atoms, and more preferably, 3 to 12 carbon atoms. The heteroarylene group refers to an arylene group containing one, two, or three heteroatoms, as atom(s) forming an aromatic ring skeleton, selected from the group consisting of N, O, P, and S, wherein at least one of the heteroatom may be oxidized or quaternarized into, for example, an N-oxide or a quaternary salt. Specific examples of such a heteroarylene group include, but are not limited to, thienylene, benzothienylene, pyridylene, pyrazinylene, pyrimidinylene, pyridazinylene, quinolinylene, quinoxalinylene, imidazolylene, furanylene, benzofuranylene, thiazolylene, isoxazolylene, benzisoxazolylene, benzimidazolylene, triazolylene, pyrazolylene, pyrrolylene, indolylene, 2-pyridonylene, 4-pyridonylene, N-alkyl-2-pyridonylene, pyrazinonylene, pyridazinonylene, pyrimidinonylene, oxazolonylene, an N-oxide of the foregoing groups, such as pyridylene N-oxide and quinolinylene N-oxide, and a quaternary salt of the foregoing groups. At least one hydrogen atom in the heteroarylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

A heteroarylenealkylene group for R may have 4 to 30 carbon atoms, preferably, 4 to 18 carbon atoms, more preferably, 4 to 12 carbon atoms. The heteroarylenealkylene group refers to a heteroarylene group that has alkylene groups substituted for some hydrogen atoms. Specific examples of such a heteroarylenealkylene group include, but are not limited to, thienylene methylene, thienylene ethylene, benzothienylene methylene, benzothienylene ethylene, pyridylene methylene, pyridylene ethylene, pyrazinylene methylene, pyrazinylene ethylene, pyrimidinylene methylene, pyrimidinylene ethylene, pyridazinylene methylene, pyridazinylene ethylene, quinolinylene methylene, quinolinylene ethylene, quinoxalinylene methylene, quinoxalinylene ethylene, imidazolylene methylene, imidazolylene ethylene, furanylene methylene, furanylene ethylene, and the like. At least one hydrogen atom in the heteroarylenealkylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

As described above, the linker X in formula (1) is a chemical bond selected from the group consisting of —O—, —CO—, —NR$_1$—, —N=N—, —S—, —C(=O)NR$_1$—, —NR$_1$C(=O)—, —SO$_2$—, —SO$_3$—, —COO—, —OCO—, —C(=S)—O—, —OC(=S)—, —CO—O—CO—, —CO—S—CO—, —CO—NR$_1$—CO—, —C(=S)—O—C(=S)—, —C(=S)—S—C(=S)—, —C(=S)—NR$_1$—C(=S)—, —O—P(=O)(OH)—O—, and —O—P(OH)—O—, where R$_1$ is a hydrogen atom or a straight or branched C$_1$–C$_6$ alkyl group.

Y in formula (1) above, which provides the benzophenone compound with wettability and the ability to stabilize a colorant, is selected from the group consisting of a substituted or unsubstituted C$_1$–C$_{20}$ alkyl group having 1 to 10 hydroxyl groups, —N(R$_1$)(R$_2$), —NHN(R$_1$) (R$_2$)—(CH$_2$)$_m$—N(R$_1$)(R$_2$), a substituted or unsubstituted C$_2$–C$_{20}$ hydroxyalkyloxyalkyl group, a substituted or unsubstituted C$_3$–C$_{10}$ lactone group, a substituted or unsubstituted C$_3$–C$_{10}$ lactame group; a substituted or unsubstituted C$_3$–C$_{30}$ heteroaryl group, a substituted or unsubstituted C$_4$–C$_{30}$ heteroarylalkyl group, a substituted or unsubstituted C$_6$–C$_{30}$ hetroarylalkenyl group, and a substituted or unsubstituted C$_3$–C$_{10}$ heterocycloalkyl group, where each of R$_1$ and R$_2$ is independently one of a hydrogen atom and a straight or branched C$_1$–C$_6$ alkyl group.

Specific examples of the substituted or unsubstituted C$_1$–C$_{20}$ alkyl group for Y in formula (1) include, but are not limited to, hydroxymethyl, hydroxyethyl, 2,3-dihydroxypropyl, and the like.

Specific examples of the group having the formula of —N($R_1$)($R_2$) for Y in formula (1) include, but are not limited to, —$NH_2$, —$NH(CH_3)$, —$N(CH_3)_2$, —$NH(CH_2CH_3)$, —$N(CH_2CH_3)_2$, and the like.

Specific examples of the group having the formula of —NHN($R_1$)($R_2$) for Y in formula (1) include, but are not limited to, —$NHNH_2$, —$NHN(CH_3)_2$, —$NHNHCH_3$, —$NHN(CH_2CH_3)_2$, —$NHNHCH_2CH_3$, and the like.

Specific examples of the group having the formula of —$(CH_2)_m$—N($R_1$)($R_2$) for Y in formula (1) include, but are not limited to, —$CH_2$—$NH_2$, —$CH_2$—$N(CH_3)_2$, —$CH_2$—$NHCH_3$, —$(CH_2)_2$—$NH_2$, —$(CH_2)_2$—$NHCH_3$, —$(CH_2)_2$—$N(CH_3)_2$, —$(CH_2)_2$—$NHCH_2CH_3$, —$(CH_2)_2$—$N(CH_2CH_3)_2$, and the like.

Specific examples of the substituted or unsubstituted $C_2$–$C_{20}$ hydroxyalkyloxyalkyl group for Y in formula (1) include, but are not limited to, —$CH_2OCH_2OH$, —$CH_2OCH_2CH_2OH$, —$CH_2CH_2OCH_2OH$, —$CH_2CH_2OCH_2CH_2OH$, —$CH_2CH_2OCH_2CH(CH_3)OH$, —$CH_2CH(CH_3)OCH_2CH_2OH$, —$CH_2CH(CH_3)OCH_2CH(CH_3)OH$, and the like.

Specific examples of a substituted or unsubstituted $C_3$–$C_{10}$ lactone group for Y in formula (1) include, but are not limited to, β-propiolactonyl, γ-butyrolactonyl δ-valerolactonyl, ε-caprolactonyl, and the like.

Specific examples of a substituted or unsubstituted $C_3$–$C_{10}$ lactame group for Y in formula (1) include, but are not limited to, β-propiolactamyl, γ-butyrolactamyl, δ-valerolactamyl, ε-caprolactamyl, and the like.

Specific examples of the substituted or unsubstituted $C_3$–$C_{30}$ heteroaryl group and the substituted or unsubstituted $C_4$–$C_{30}$ heteroarylalkyl group for Y in formula (1) are the same as those for $Y_2$ or $Y_3$ in formula (1) described above.

The substituted or unsubstituted hetroarylalkenyl group for Y in formula (1) may have 6 to 30 carbon atoms, preferably, 6 to 18 carbon atoms, and more preferably, 6 to 12 carbon atoms. Specific examples of such a heteroarylalkenyl group include, but are not limited to, thienylethenyl, benzothienylethenyl, pyridylethenyl, pyrazinylethenyl, pyrimidinylethenyl, pyridazinylethenyl, quinolinylethenyl, quinoxalinylethenyl, imidazolylethenyl, furanylethenyl, benzofuranylethenyl, thiazolylethenyl, isoxazolylethenyl, benzisoxazolylethenyl, benzimidazolylethenyl, triazolylethenyl, and the like.

The substituted or unsubstituted heterocycloalkyl group for Y in formula (1) may have 3 to 10 carbon atoms, preferably, 3 to 8 carbon atoms, and more preferably, 3 to 6 carbon atoms. A specific example of such a heterocycloalkyl group includes, but is not limited to, thiazolydinyl.

Specific examples of the benzophenone derivative of formula (1) above include benzophenone compounds having formulas (3) through (11) below.

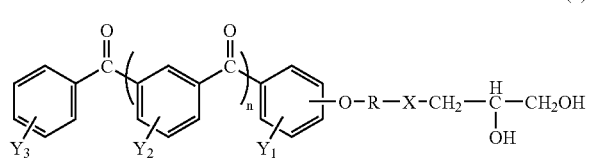
(3)

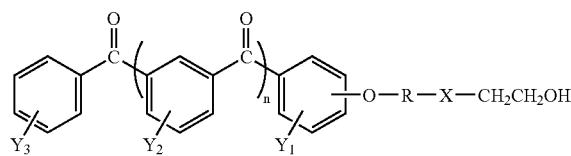
(4)

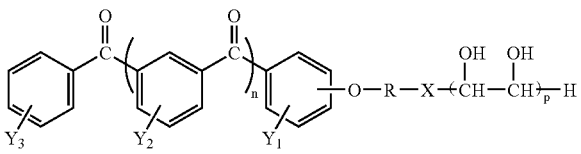
(5)

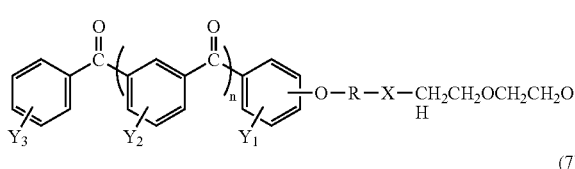
(6)

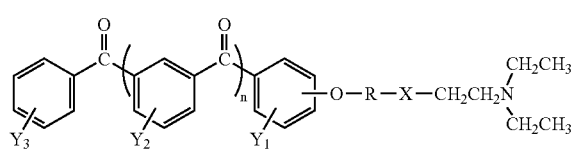
(7)

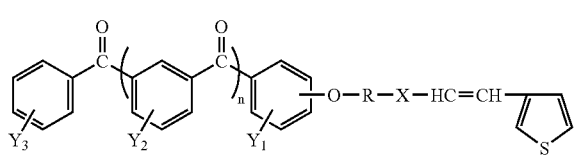
(8)

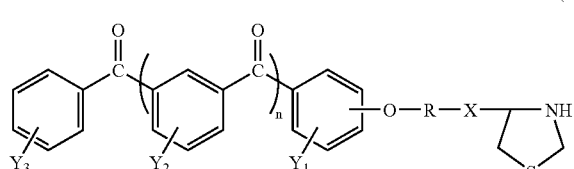
(9)

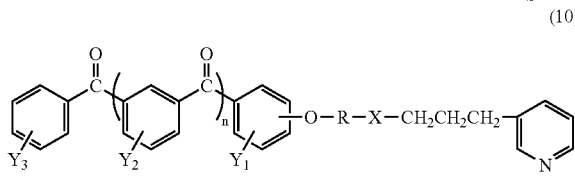
(10)

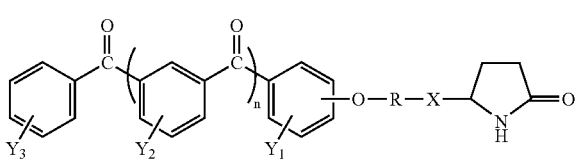
(11)

In formulas (3) through (11) above, $Y_1$, $Y_2$, $Y_3$, R, n, and X are the same as in formula (1) above.

hereinafter, a lightfast ink composition that includes the above benzophenone derivative of formula (1) according to embodiments of the present invention will be described in detail.

An ink composition according to an embodiment of the present invention includes a functional additive comprising the benzophenone compound of formula (1) above to improve lightfastness and wettablity and the ability to stabilize a colorant. An ink composition according to an embodiment of the present invention may include a colorant, the bezophenone compound of formula (1), and an aqueous medium.

In the ink composition according to an embodiment of the present invention, the amount of the colorant may be in the range of 0.1–20 parts by weight, and preferably, 0.5–15 parts by weight, with respect to 100 parts by weight of the ink composition. If the amount of the colorant is less than 0.1 parts by weight, the color strength is ineffective in forming color images. If the amount of the colorant is greater than 20 parts by weight, nozzles clog due to excess colorant.

Both dye and pigment may be used as colorants in the ink composition according to embodiments of the present invention. Specific examples of a dye that may be used in the present invention include, but are not limited to, C.I. DIRECT BLACK Nos. 9, 17, 19, 22, 32, 51, 56, 91, 94, 97, 166, 168, 173, and 199; C.I. DIRECT BLUE Nos. 1, 10, 15, 22, 77, 78, 80, 200, 201, 202, 203, 207, and 211; C.I. DIRECT RED Nos. 2, 4, 9, 23, 31, 39, 63, 72, 83, 84, 89, 111, 173, 177, 184, and 240; and C.I. DIRECT YELLOW Nos. 8, 9, 11, 12, 27, 28, 29, 33, 35, 39, 41, 44, 50, 53, and 58. Other direct dyes, disperse dyes, basic dyes, acidic dyes, azo dyes, and the like, may be used. Both inorganic and organic pigments may be used. Specific examples of a pigment that may be used in the present invention include, but are not limited to, carbon black, graphite, vitreous carbon, activated charcoal, activated carbon, anthraquinones, phthalocyanine blue, phthalocyanine green, diazos, monoazos, pyranthrones, perylenes, quinacridone, and indigoid pigments.

The particle size of pigments significantly affects wettability, color strength, and glossiness. A pigment used as the colorant in the present invention may have a particle diameter that is small enough to pass through 10–50 μm nozzles.

In the ink composition according to embodiments of the present invention, the amount of the benzophenone derivative of formula (1) is in the range of 0.1–40 parts by weight, preferably, 0.5–20 parts by weight, and more preferably, 1–10 parts by weight, with respect to 100 parts by weight of the ink composition. If the amount of the benzophenone derivative is less than 0.1 parts by weight, improvements in lightfastness, wettability, and colorant stabilization are trivial. If the amount of the benzophenone derivative is greater than 40 parts by weight, the ink composition is too thick.

In the ink composition according to an embodiment of the present invention, the colorant and the benzophenone derivative of formula (1) are dissolved or dispersed in an aqueous medium.

The aqueous medium may be water alone or a mixture of 5–50% by weight of an organic solvent and 50–95% by weight of water. A mixture of 5–35% by weight of an organic solvent and 65–95% by weight of water is preferred. When a mixture of water and an organic solvent is used as the aqueous medium, the ratio of water and the organic solvent may be varied depending on various factors, for example, desired characteristics, such as the viscosity, surface tension, drying speed, and the like, of the ink composition. Such characteristics of ink compositions vary depending on the printing methods of printers and the types of printing media.

Examples of a suitable organic solvent include, but are not limited to, alcohols, such as methyl alcohol, ethyl alcohol, n-propyl alcohol, isopropyl alcohol, n-butyl alcohol, sec-butyl alcohol, t-butyl alcohol, isobutyl alcohol, and the like; ketones, such as acetone, methyl ethyl ketone, diacetone alcohol, and the like; esters, such as methyl acetate, ethyl acetate, ethyl lactate, and the like; polyhydric alcohols, such as ethylene glycol, diethylene glycol, triethylene glycol, propylene glycol, butylene glycol, 1,4-butane diol, 1,2,4-butane triol, 1,5-pentane diol, 1,2,6-hexane triol, hexylene glycol, glycerol, glycerol ethoxylate, trimethylolpropane ethoxylate, and the like; ethers, such as ethylene glycol monomethyl ether, ethylene glycol monoethyl ether, diethylene glycol methyl ether, diethylene glycol ethyl ether, triethylene glycol monomethyl ether, triethylene glycol monoethyl ether, and the like; nitrogen-containing compounds, such as 2-pyrrolidone, N-methyl-2-pyrrolidone, and the like; and sulfur-containing compounds, such as dimethyl sulfoxide, tetramethylene sulfone, and thioglycol, and the like.

Alternatively, the ink composition according to an embodiment of the present invention may further include an additive, for example, a dispersant, a viscosity adjuster, a surfactant, and the like.

In particular, when a pigment or a water-insoluble dye is used as the colorant, at least one dispersant may be added to the ink composition to improve the dispersion stability of the colorant. Any dispersants, including non-complex structure, lower molecular weight dispersants, and larger molecular weight dispersants, such as block copolymers, which do not limit the physical properties, stability, and functionality of the ink composition, may be used without limitation.

Specific examples of lower molecular weight, simpler structure dispersants include, but are not limited to, polyvinyl alcohol (PVA), cellulosics, ethylene oxide modified phenols, an ethylene oxide/propylene oxide polymer, a sodium polyacrylate solution (TEGO, disperse 715W), a modified polyacryl resin solution (TEGO, disperse 735W), a solution of alkylol ammonium salt of a low molecular weight carboxylic polymer (BYK-CHEMIE, Disperbyk), a solution of alkylol ammonium of a multifunctional polymer (BYK-CHEMIE, Disperbyk-181), and an mixture of the foregoing dispersants.

Specific examples of complex, larger molecular weight dispersants include, but are not limited to, siloxanes, such as a polyester siloxane copolymer (TEGO, Wet KL 245/Wet 260), and hydrophilic polymers having the structure of AB or BAB, where A is a hydrophobic homopolymer or copolymer block of an unsubstituted or substituted $C_1$–$C_{20}$ acrylic monomer and B is a hydrophilic polymer or copolymer block of a unsubstituted or substituted $C_1$–$C_{30}$ acrylic polymer. More specific examples of the complex, larger molecular weight dispersants include, but are not limited to, an acrylic acid/acrylate copolymer, a methacrylic acid/methacrylate copolymer, an acrylic acid/polydialkylsiloxane/acrylate block copolymer, and a mixture of the foregoing polymers.

The amount of the dispersant may be in the range of 0.1–20 parts by weight, preferably, 0.1–10 parts by weight, and more preferably, 0.1–5 parts by weight, with respect to 100 parts by weight of the ink composition.

The viscosity adjuster of the ink composition adjusts the viscosity of the ink composition for smoother jetting. Specific examples of such a viscosity adjuster include, but are not limited to, casein, hydroxymethylcellulose, hydroxyethylcellulose, carboxymethylcellulose, and the like. The amount of the viscosity adjuster may be in the range of 0.1–5 parts by weight with respect to 100 parts by weight of the ink composition.

The amount of the surfactant may be in the range of 0.1–5 parts by weight with respect to 100 parts by weight of the ink composition. The surfactant of the ink composition affects the surface tension of the composition such that the ink composition is more stably jetted through a nozzle. An anionic surfactant or a nonionic surfactant may be used.

Examples of an anionic surfactant that may be used in the present invention include, but are not limited to, a salt of alkylcarboxylic acid having 2 to 1,000 carbon atoms, preferably, 10 to 200 carbon atoms, a salt of sulfonic acid having 2 to 1,000 carbon atoms, preferably, 10 to 200 carbon atoms, a salt of alkyl sulfonic acid ester having 2 to 1,000 carbon atoms, preferably, 10 to 200 carbon atoms, a salt of alkyl sulfonic acid having 2 to 1,000 carbon atoms, preferably, 10 to 200 carbon atoms, a salt of alkylaryl sulfonic acid having 7 to 1,000 carbon atoms, preferably, 10 to 200 carbon atoms, and a mixture of the foregoing salts.

Examples of a nonionic surfactant that may be used in the present invention include, but are not limited to, polyoxyethylene alkyl ether having a $C_1$–$C_{1000}$, preferably, $C_{10}$–$C_{200}$, alkyl group, polyoxyethylene alkyl phenyl ether having a $C_1$–$C_{1000}$, preferably, $C_{10}$–$C_{200}$, alkyl group, polyoxyethylene secondary alkyl ether, a polyoxyethylene-oxypropylene block copolymer, polyglycerin fatty acid ester, sorbitan fatty acid ester, and a mixture of the foregoing materials.

Alternatively, the ink composition according to an embodiment of the present invention may further include an acid or a base to increase the solubility of additives in the solvent and stabilize the pigment in the ink composition. The amount of the acid or base may be in the range of 0.1–20 parts by weight, preferably, 0.1–5 parts by weight, with respect to 100 parts by weight of the ink composition.

In an ink composition according to an embodiment of the present invention, the total amount of at least one additive selected from the group consisting of a dispersant, a viscosity adjuster, and a surfactant may be in the range of 0.5–40 parts by weight with respect to 100 parts by weight of the ink composition.

A method of preparing the above ink composition, according to an embodiment of the present invention, will now be described.

A common colorant, the benzophenone derivative of formula (1) above, which has wettability and the ability to stabilize the colorant, and other additives, for example, a dispersant, a viscosity adjuster, a surfactant, and the like, are mixed together in an aqueous medium and thoroughly stirred to obtain a homogeneous composition. This composition is passed through a filter having a pore size of about 0.45–0.8 μm to obtain an ink composition according to an embodiment of the present invention.

The benzophenone derivative of formula (1) above according to an embodiment of the present invention may have various, non-limiting applications, for example, in liquid toner compositions, dry toner compositions, various paints, coating solutions, and the like, in addition to ink compositions.

The present invention will be described in greater detail with reference to the following examples. The following examples are for illustrative purposes and are not intended to limit the scope of the invention.

SYNTHESIS EXAMPLE 1

2-hydroxy-4-(4-carboxy)phenyloxybenzophenone was Synthesized According to Reaction Scheme (5) Below Reaction scheme (5)

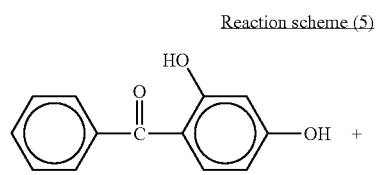

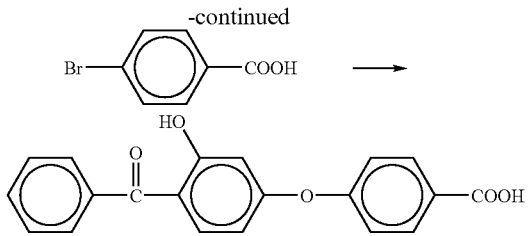

A 250-mL round-bottomed flask equipped with a reflux condenser was charged with 150 mL of DMF and 10.7 g of 2,4-dihydxoxybenzophenone, and 1.2 g of sodium hydroxide was added while supplying nitrogen into the flask and stirring. 10 g of 4-bromobenzoic acid was slowly added into the mixture, heated slowly to about 60° C. while stirring it, and reacted for 5 hours. The reaction mixture was cooled to room temperature, and excess distilled water was added to the reaction product to precipitate it. Precipitates were filtered, washed several times with distilled water, and recrystallized using a solvent mixture of chloroform and ethanol to provide 9.5 g of 2-hydroxy-4-(carboxy)phenyloxybenzophenone.

SYNTHESIS EXAMPLE 2

2-hydroxy-4-(8-carboxy)octyloxybenzophenone was Synthesized According to Reaction Scheme (6) Below Reaction scheme (6)

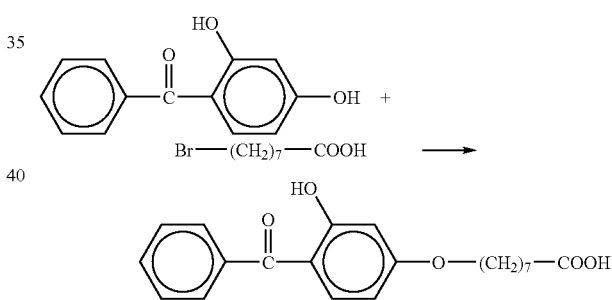

10 g of 2-hydroxy-4-(8-carboxy)octyloxybenzophenone was synthesized in the same manner as in Synthesis Example 1, except that 11.5 g of 8-bromooctanoic acid was used instead of 10 g of 4-bromobenzoic acid.

SYNTHESIS EXAMPLE 3

2-hydroxy-4-(4-hydroxy)phenyloxybenzophenone was Synthesized According to Reaction Scheme (7) Below Reaction scheme (7)

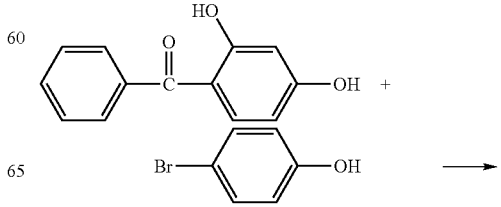

-continued

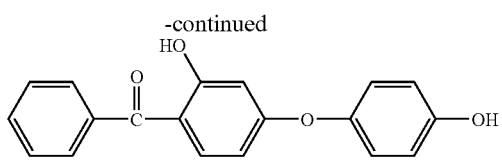

9.7 g of 2-hydroxy-4-(4-carboxy)phenyloxybenzophenone was synthesized in the same manner as in Synthesis Example 1, except that 8.7 g of bromophenol was used instead of 10 g of 4-bromobenzoic acid.

SYNTHESIS EXAMPLE 4

2-hydroxy-4-(6-hydroxy)hexyloxybenzophenone was Synthesized According to Reaction Scheme (8) Below

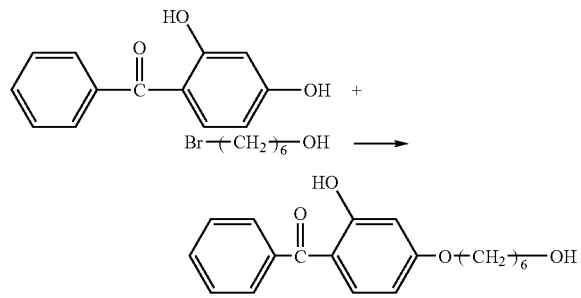

10.6 g of 2-hydroxy-4-(6-hydroxy)hexyloxybenzophenone was synthesized in the same manner as in Synthesis Example 1, except that 9.1 g of 6-bromo-1-hexanol was used instead of 10 g of 4-bromobenzoic acid.

SYNTHESIS EXAMPLE 5

2-hydroxy-4-(4-amino)phenyloxybenzophenone was Synthesized According to Reaction Scheme (9) Below

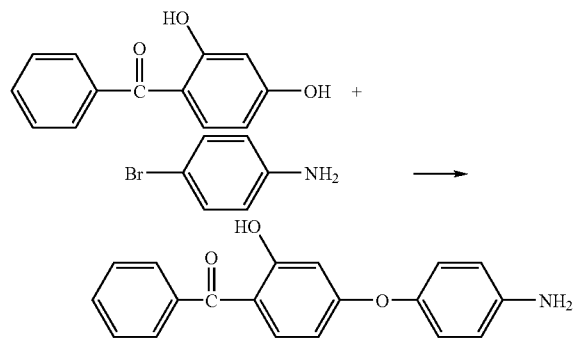

10.3 g of 2-hydroxy-4-(4-amino)phenyloxybenzohenone was synthesized in the same manner as in Synthesis Example 1, except that 8.6 g of 4-bromoaniline was used instead of 10 g of 4-bromobenzoic acid.

SYNTHESIS EXAMPLE 6

A lightfast colorant of formula (12) below was synthesized by reacting the benzophenone derivative obtained in Synthesis Example 1 with glycerol.

A 250-mL round-bottomed flask equipped with a reflux condenser was charged with 100 mL of ethyl acetate and 8.4 g of the 2-hydroxy-4-(4-carboxy)phenyloxy-benzophenone and stirred to dissolve the benzophenone compound. 2.6 g of glycerol was added into the round-bottomed flask. 20 mL of conc. sulfuric acid was slowly added together with one or two boiling chips into the mixture and refluxed for 12 hours or longer. The reaction product was cooled to room temperature, and excess methanol was added to precipitate a desired crystalline compound. To remove unreacted products, the crystalline compound was dissolved in dimethylsulfoxide (DMSO) and precipitated with methanol. The crystalline precipitates were filtered and dried in a 60° C. oven to provide 7.9 g of the benzophenone compound of formula (12).

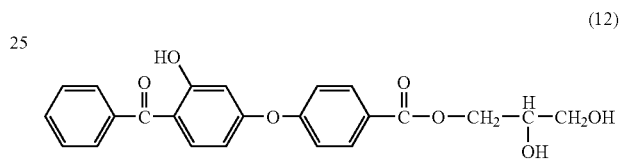

SYNTHESIS EXAMPLE 7

7.3 g of a benzophenone compound of formula (13) below was synthesized from 8.9 g of the 2-hydroxy-4(-8-carboxy) octyloxybenzophenone obtained in Synthesis Example 2 and 1.7 g of ethylene glycol in the same manner as in Synthesis Example 6.

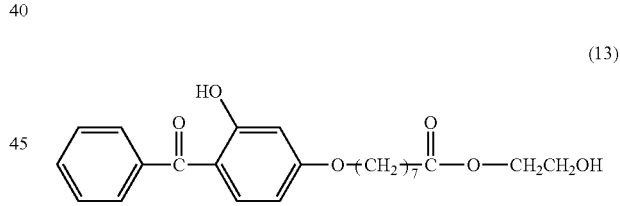

SYNTHESIS EXAMPLE 8

8.1 g of a benzophenone compound of formula (14) below was synthesized from 8.9 g of the 2-hydroxy-4(-8-carboxy) octyloxybenzophenone obtained in Synthesis Example 2 and 2.8 g of diethylene glycol in the same manner as in Synthesis Example 6.

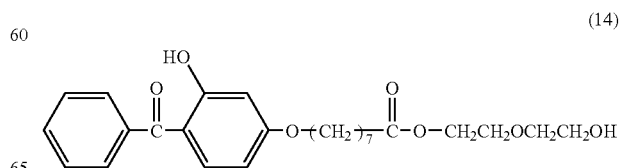

SYNTHESIS EXAMPLE 9

8.1 g of a benzophenone compound of formula (16) below was synthesized from 8.9 g of the 2-hydroxy-4-(-8-carboxy) octyloxybenzophenone obtained in Synthesis Example 2 and 6.7 g of a polyol compound of formula (15) below in the same manner as in Synthesis Example 6.

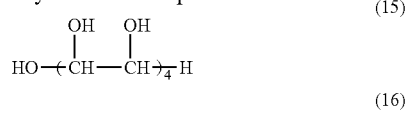

(15)

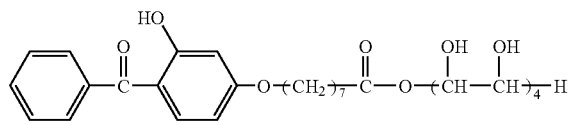

(16)

SYNTHESIS EXAMPLE 10

A benzophenone derivative of formula (17) below was synthesized by reacting the 2-hydroxy-4-(4-hydroxy)phenyloxybenzophenone obtained in Synthesis Example 3 with 3-(diethylamino)propionic acid.

A 250-mL round-bottomed flask equipped with a reflux condenser was charged with 50 mL of DMSO and 4.6 g of 3-(diethylamino)propionic acid and stirred to dissolve the 3-(diethylamino)propionic acid. 3.0 g of $SOCl_2$ was added to the mixture and reacted at room temperature for 1 hour or longer to provide a solution (A).

A solution (B) of 7.7 g of the 2-hydroxy-4-(4-hydroxy) phenyloxybenzo-phenone obtained in Synthesis Example 3 in 50 mL of DMSO was added to the solution (A) together with one or two boiling chips and reacted at 80° C. for 6 hours or longer.

The reaction product was cooled to room temperature, and excess methanol was added to precipitate a desired crystalline compound. The crystalline precipitates were filtered. To remove unreacted products, the crystalline compound was dissolved in DMSO and precipitated with methanol. The crystalline precipitates were filtered and dried in a 60° C. oven to provide 8.5 g of the benzophenone compound of formula (17).

(17)

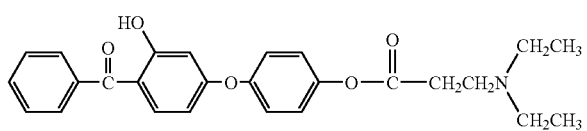

SYNTHESIS EXAMPLE 11

7.3 g of a benzophenone compound of formula (18) below was synthesized from 7.9 g of the 2-hydroxy-4-(6-hydroxy) hexyloxybenzophenone obtained in Synthesis Example 4 and 3.0 g of 3,4-dihydroxybutyric acid in the same manner as in Synthesis Example 10.

(18)

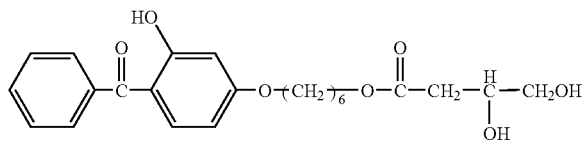

SYNTHESIS EXAMPLE 12

A benzophenone derivative of formula (19) below was synthesized by reacting the 2-hydroxy-4-(6-hydroxy)hexyloxybenzophenone obtained in Synthesis Example 4 with 3-(3-thienyl)acrylic acid.

A 250-mL round-bottomed flask was charged with 100 mL of ethyl acetate, 7.9 g of the 2-hydroxy-4-(6-hydroxy) hexyloxybenzophenone obtained in Synthesis Example 4, and 3.9 g of 3-(3-thienyl)acrylic acid and stirred to dissolve the reactants. 10 mL of conc. sulfuric acid was slowly added together with one or two boiling chips into the mixture and refluxed for 12 hours or longer. The reaction product was washed with distilled water to extract the organic phase. The organic phase was concentrated and recrystallized to provide 9.1 g of the benzophenone compound of formula (19).

(19)

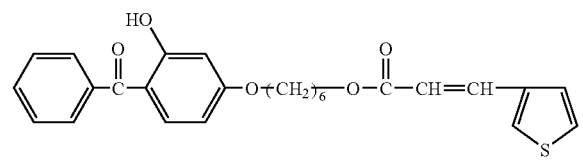

SYNTHESIS EXAMPLE 13

7.6 g of a benzophenone compound of formula (20) below was synthesized from 7.6 g of the 2-hydroxy-4-(4-amino) phenyloxybenzophenone obtained in Synthesis Example 5 and 3.7 g of thiazolidine-4-carboxylic acid in the same manner as in Synthesis Example 12.

(20)

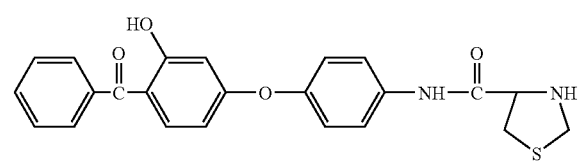

SYNTHESIS EXAMPLE 14

9.1 g of a benzophenone compound of formula (21) below was synthesized from 8.9 g of the 2-hydroxy-4-(8-carboxyl) octyloxybenzophenone obtained in Synthesis Example 2 and 3.6 g of 2-pyridinepropanol in the same manner as in Synthesis Example 12.

(21)

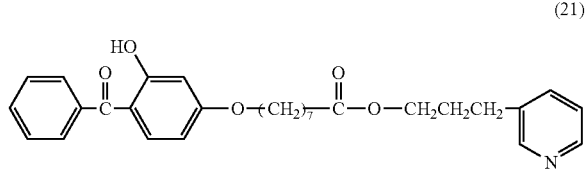

SYNTHESIS EXAMPLE 15

7.7 g of a benzophenon compound of formula (22) below was synthesized from 7.6 g of the 2-hydroxy-4-(4-amino) phenyloxybenzophenone obtained in Synthesis Example 5 and 3.5 g of 2-pyrrolidone-5-carboxylic acid in the same manner as in Synthesis Example 12.

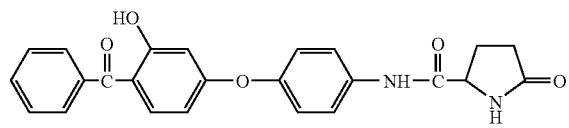

(22)

EXAMPLE 1

INK COMPOSITION

| COMPONENT | CONTENT |
| --- | --- |
| Colorant (C.I. DIRECT BLACK 9) | 4.0 g |
| Water | 77.0 g |
| Isopropyl alcohol | 3.0 g |
| Ethylene glycol | 8.0 g |
| Benzophenone derivative of formula (12) | 8.0 g |

The above-listed components were mixed together and stirred for about 30 minutes or longer to obtain a homogeneous composition. This composition was passed through a 0.45-μm filter to provide an ink composition according to an embodiment of the present invention.

EXAMPLE 2

An ink composition according to an embodiment of the present invention was prepared in the same manner as in Example 1, except that the benzophenone derivative of formula (13) was used instead of the benzophenone derivative of formula (12).

EXAMPLE 3

An ink composition according to an embodiment of the present invention was prepared in the same manner as in Example 1, except that the benzophenone derivative of formula (14) was used instead of the benzophenone derivative of formula (12).

EXAMPLE 4

An ink composition according to an embodiment of the present invention was prepared in the same manner as in Example 1, except that the benzophenone derivative of formula (16) was used instead of the benzophenone derivative of formula (12).

EXAMPLE 5

An ink composition according to an embodiment of the present invention was prepared in the same manner as in Example 1, except that the benzophenone derivative of formula (17) was used instead of the benzophenone derivative of formula (12).

EXAMPLE 6

An ink composition according to an embodiment of the present invention was prepared in the same manner as in Example 1, except that the benzophenone derivative of formula (18) was used instead of the benzophenone derivative of formula (12).

EXAMPLE 7

An ink composition according to an embodiment of the present invention was prepared in the same manner as in Example 1, except that the benzophenone derivative of formula (19) was used instead of the benzophenone derivative of formula (12).

EXAMPLE 8

An ink composition according to an embodiment of the present invention was prepared in the same manner as in Example 1, except that the benzophenone derivative of formula (20) was used instead of the benzophenone derivative of formula (12).

EXAMPLE 9

An ink composition according an embodiment of to the present invention was prepared in the same manner as in Example 1, except that the benzophenone derivative of formula (21) was used instead of the benzophenone derivative of formula (12).

EXAMPLE 10

An ink composition according to an embodiment of the present invention was prepared in the same manner as in Example 1, except that the benzophenone derivative of formula (22) was used instead of the benzophenone derivative of formula (12).

Comparative Example 1

An ink composition was prepared in the same manner as in Example 1, except that glycerol was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

Comparative Example 2

An ink composition was prepared in the same manner as in Example 1, except that ethylene glycol was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

Comparative Example 3

An ink composition was prepared in the same manner as in Example 1, except that the polyol compound of formula (15) was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

Comparative Example 4

An ink composition was prepared in the same manner as in Example 1, except that 3,4-dihydroxybutylic acid was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

Comparative Example 5

An ink composition was prepared in the same manner as in Example 1, except that 3-(3-thienyl) acrylic acid was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

Comparative Example 6

An ink composition was prepared in the same manner as in Example 1, except that thiazoline-4-carboxylic acid was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

Comparative Example 7

An ink composition was prepared in the same manner as in Example 1, except that 2-pyridinepropanol was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

Comparative Example 8

An ink composition was prepared in the same manner as in Example 1, except that 2-pyrolidone-5-carboxylic acid was used instead of the benzophenone derivative of formula (12). 0.5 g of IRGANOX 245DW (available from CIBA SPECIALTY CHEMICALS, Switzerland) acting as a lightfast stabilizer was further added, and the amount of water was reduced by 0.5 g.

The properties of the ink compositions prepared in Examples 1 through 10 and Comparative Examples 1 through 8 were evaluated as follows.

Long-Term Storage Stability 100 mL of samples of the ink compositions prepared in Examples 1 through 10 and Comparative Examples 1 through 8 were portioned into respective heat-resistant glass bottles. The glass bottles were sealed and stored in a 60° C. water bath for 2 months. It was observed whether precipitates appeared in the bottles. The results are shown in Table 1. In Table 1, 0 indicates that no precipitates appear, and x indicates that a precipitate appears.

TABLE 1

| | Example | Comparative Example |
|---|---|---|
| No. | 1 2 3 4 5 6 7 8 9 10 | 1 2 3 4 5 6 7 8 |
| Result | 0 0 0 0 0 0 0 0 0 0 | x x x x x x x x |

As shown in Table 1, for the ink compositions prepared in Examples 1 through 10, which contain the benzophenone derivative of formula (1), no precipitates appear, indicating that the ink compositions according to embodiments of the present invention have more effective long-term storage stability than the ink compositions of Comparative Examples 1 through 8 that do not contain the benzophenone derivative.

Lightfastness Test

2×2 cm solid patterns were printed using the ink compositions of Examples 1 through 10 and Comparative Examples 1 through 8 and an ink jet printer (MJC 1130i, available from SAMSUNG ELECTRONICS CO.). The printed results were exposed to light for 100 hours in a Q-SUN Xenon Test Chamber. Optical density (OD) was measured before and after light exposure, and A values (lightfastness values) were calculated using the following equation. Lightfastness was evaluated as effective (0) for $A \geq 90$, moderate ($\Delta$) for $75 \leq A < 90$, and poor (X) for $A<75$. The results are shown in Table 2.

$A=OD$ after exposure/$OD$ before exposure×100(%)

TABLE 2

| | Example | Comparative Example |
|---|---|---|
| No. | 1 2 3 4 5 6 7 8 9 10 | 1 2 3 4 5 6 7 8 |
| Result | 0 0 0 0 0 0 0 0 0 0 | $\Delta$ 0 0 $\Delta$ $\Delta$ 0 0 $\Delta$ |

As shown in Table 2, the ink compositions prepared in Examples 1 through 10, which contain the benzophenone derivative of formula (1), have effective lightfastness at A values of 90% or more. However, the ink compositions prepared in Comparative Examples 1, 4, 5, and 8, which do not contain the benzophenone derivative, have lightfastness values of less then 90%. Evidently, the ink compositions according to embodiments of the present invention, which contain the benzophenone derivative of formula (1), have improved lightfastness compared to the conventional ink compositions.

As described above, the benzophenone derivative of formula (1) above according to embodiments of the present invention may exhibit effective ultraviolet (UV) light absorption capacity, effective wettability, and ability to stabilize a colorant. Therefore, when the benzophenone derivative of formula (1) is added to an ink composition, the lightfastness, wettability, and long-term storage stability of the ink composition are improved, and there is no need to add an additional lightfast enhancer.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A lightfast ink composition comprising;
a colorant;
an aqueous medium; and
at least one benzophenone derivative of formula (1) below:

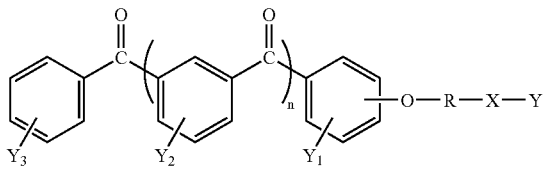

wherein $Y_1$ is one selected from the group consisting of a H, a OH, an $N(R_1)(R_2)$, a SH, and a $C_1$–$C_{30}$ heteroalkyl group;

each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —O—, —CO—, —$NR_1$—, —N=N—, —S—, —C(=O)$NR_1$—, —$NR_1$C(=O)—, —$SO_2$—, —$SO_3$—, —COO—, —OCO—, —C(=S)—O—, —OC(=S)—, —CO—O—CO—, —CO—S—CO—, —CO—$NR_1$—CO—, —C(=S)—O—C(=S)—, —C(=S)—S—C(=S)—, —C(=S)—$NR_1$—C(=S)—, —O—P(=O)(OH)—O—, and —O—P(OH)—O—;

Y is selected from the group consisting of a substituted or unsubstituted $C_1$–$C_{20}$ alkyl group having 1 to 10 hydroxyl groups, —$N(R_1)(R_2)$, —$NHN(R_1)(R_2)$, —$(CH_2)_m$—$N(R_1)(R_2)$, a substituted or unsubstituted $C_2$–$C_{20}$ hydroxyalkyloxyalkyl group, a substituted or unsubstituted $C_3$–$C_{10}$ lactone group, a substituted or unsubstituted $C_3$–$C_{10}$ lactame group; a substituted or unsubstituted $C_3$–$C_{30}$ heteroaryl group, a substituted or unsubstituted $C_4$–$C_{30}$ heteroarylalkyl group, a substituted or unsubstituted $C_6$–$C_{30}$ heteroarylalkenyl group, and a substituted or unsubstituted $C_3$–$C_{10}$ heterocycloalkyl group; and each of $R_1$ and $R_2$ is independently one of a hydrogen atom and a $C_1$–$C_6$ alkyl group; and m and n are independently integers from 0 to 6.

2. The lightfast ink composition of claim 1, wherein an amount of the colorant is in a range of 0.1–20 parts by weight with respect to 100 parts by weight of the ink composition.

3. The lightfast ink composition of claim 1, wherein an amount of the benzophenone derivatives is in a range of 0.1–40 parts by weight with respect to 100 parts by weight of the ink composition.

4. The lightfast ink composition of claim 1, wherein the aqueous medium is water or a mixture of 5–10% by weight of an organic solvent and 50–95% by weight of water.

5. The lightfast ink composition of claim 4, wherein the organic solvent is selected from the group consisting of methyl alcohol, ethyl alcohol, n-propyl alcohol, isopropyl alcohol, n-butyl alcohol, sec-butyl alcohol, t-butyl alcohol, isobutyl alcohol, acetone, methyl ethyl ketone, diethyl ketone, diacetone alcohol, methyl acetate, ethyl acetate, ethyl lactate, ethylene glycol, diethylene glycol, triethylene glycol, propylene glycol, butylene glycol, 1,4-butane diol, 1,2,4-butane triol, 1,5-pentane diol, 1,2,6-hexane triol, hexylene glycol, glycerol, glycerol ethoxylate, trimethylolpropane ethoxylate, ethylene glycol monomethyl ether, ethylene glycol monoethyl ether, diethylene glycol methyl ether, diethylene glycol ethyl ether, triethylene glycol monomethyl ether, triethylene glycol monoethyl ether, 2-pyrrolidone, N-methyl-2-pyrrolidone, dimethyl sulfoxide, tetramethylene sulfone, and thioglycol.

6. The lightfast ink composition of claim 1, further comprising at least one additive selected from the group consisting of a dispersant, a viscosity adjuster, and a surfactant, wherein an amount of the at least one additive is in a range of 0.5–40 parts by weight with respect to 100 parts by weight of the ink composition.

7. The lightfast ink composition of claim 1, wherein at least one benzophenone derivative has the formula (12):

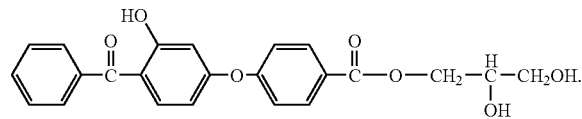

8. The lightfast ink composition of claim 1, wherein at least one benzophenone derivative has the formula (13):

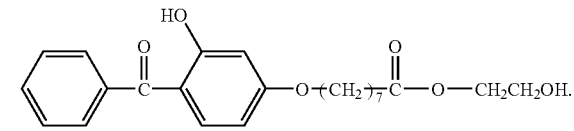

9. The lightfast ink composition of claim 1, wherein at least one benzophenone derivative has the formula (14):

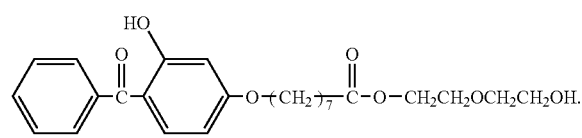

10. The lightfast ink composition of claim 1, wherein at least one benzophenone derivative has the formula (16):

(16)

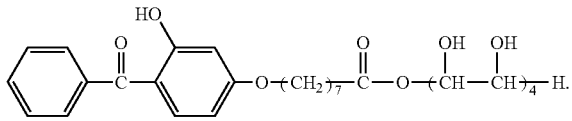

11. The lightfast ink composition of claim 1, wherein at least one benzophenone derivative has the formula (17):

(17)

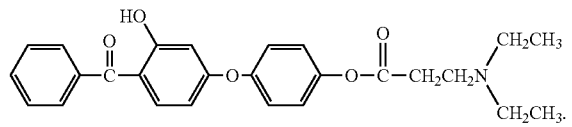

12. The lightfast ink composition of claim 1, wherein at least one benzophenone derivative has the formula (18):

(18)

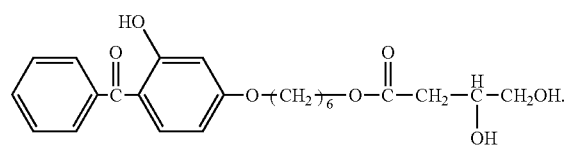

13. The lightfast ink composition of claim 1, wherein at least one benzophenone derivative has the formula (19):

(19)

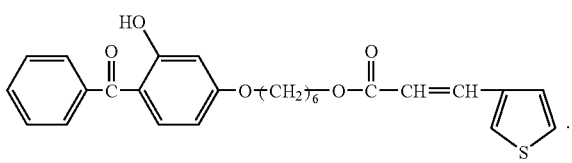

14. The lightfast ink composition of claim 1, wherein at least one benzophenone derivative has the formula (20):

(20)

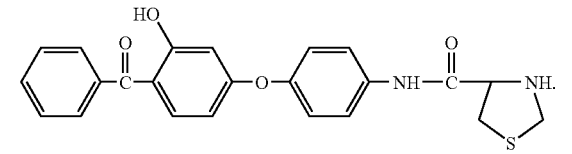

15. The lightfast ink composition of claim 1, wherein at least one benzophenone derivative has the formula (21):

(21)

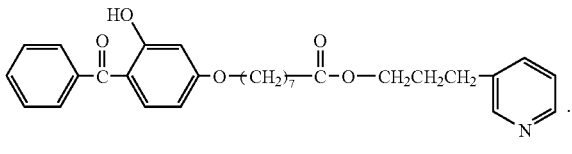

16. The lightfast ink composition of claim 1, wherein at least one benzophenone derivative has the formula (22):

(22)

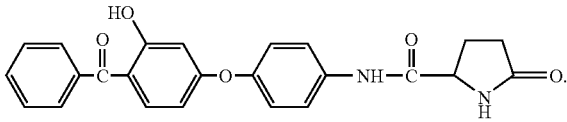

17. An ink composition comprising:
a colorant;
an aqueous medium; and
a lightfast additive comprising a benzophenone moiety for lightfastness and a wettability/stabilizing moiety to provide wettability and to stabilize a colorant, wherein the two moieties are covalently bonded.

18. The ink composition of claim 17, wherein the covalently bonded benzophenone and wettability/stabilizing moieties are represented by formula (1) below:

(1)

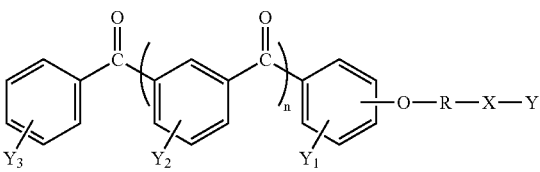

wherein $Y_1$ is one selected from the group consisting of a H, a OH, an $N(R_1)(R_2)$, a SH, and a $C_1$–$C_{30}$ heteroalkyl group;

each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —O—, —CO—, —$NR_1$—, —N=N—, —S—, —C(=O)$NR_1$—, —$NR_1$C(=O)—, —$SO_2$—, —$SO_3$—, —COO—, —OCO—, —C(=S)—O—, —OC(=S)—, —CO—O—CO—, —CO—S—CO—, —CO—$NR_1$—CO—, —C(=S)—O—O(=S)—, —C(=S)—S—O(=S)—, —C(=S)—$NR_1$—C(=S)—, —O—P(=O)(OH)—O—, and —O—P(OH)—O—;

Y is selected from the group consisting of a substituted or unsubstituted $C_1$–$C_{20}$ alkyl group having 1 to 10 hydroxyl groups, —$N(R_1)(R_2)$, —$NHN(R_1)(R_2)$, —$(CH_2)_m$—$N(R_1)(R_2)$, a substituted or unsubstituted $C_2$–$C_{20}$ hydroxyalkyloxyalkyl group, a substituted or unsubstituted $C_3$–$C_{10}$ lactone group, a substituted or unsubstituted $C_3$–$C_{10}$ lactame group; a substituted or unsubstituted $C_3$–$C_{30}$ heteroaryl group, a substituted or unsubstituted $C_4$–$C_{30}$ heteroarylalkyl group, a substituted or unsubstituted $C_6$–$C_{30}$ heteroarylalkenyl group, and a substituted or unsubstituted $C_3$–$C_{10}$ heterocycloalkyl group; and each of $R_1$ and $R_2$ is independently one of a hydrogen atom and a $C_1$–$C_6$ alkyl group; and m and n are independently integers from 0 to 6.

* * * * *

UNITED STATES PATENT AND TRADEMARK OFFICE
CERTIFICATE OF CORRECTION

| | | |
|---|---|---|
| PATENT NO. | : 7,125,442 B2 | Page 1 of 1 |
| APPLICATION NO. | : 10/851161 | |
| DATED | : October 24, 2006 | |
| INVENTOR(S) | : Kyung-hoon Lee et al. | |

It is certified that error appears in the above-identified patent and that said Letters Patent is hereby corrected as shown below:

Column 28, Line 61, change "–C(=S)–O–O(=S)–," to -- –C(=S)–O–C(=S)–, --.

Column 28, Line 62, change "–C(=S)–S–O(=S)–," to -- –C(=S)–S–C(=S)–, --

Signed and Sealed this

Sixth Day of March, 2007

JON W. DUDAS
*Director of the United States Patent and Trademark Office*